United States Patent [19]
Hirth

[11] Patent Number: 5,942,385
[45] Date of Patent: Aug. 24, 1999

[54] METHOD FOR MOLECULAR DIAGNOSIS OF TUMOR ANGIOGENESIS AND METASTASIS

[75] Inventor: Klaus Peter Hirth, San Francisco, Calif.

[73] Assignee: Sugen, Inc., South San Francisco, Calif.

[21] Appl. No.: 08/624,858

[22] Filed: Mar. 21, 1996

[51] Int. Cl.$^6$ .......................... C12Q 1/00; G01N 33/53; C12N 5/08; C07H 21/04

[52] U.S. Cl. ................................. 435/4; 435/6; 435/7.1; 435/7.92; 435/91.2; 435/366; 536/23.1

[58] Field of Search .......................... 435/4, 6, 7.1, 7.23, 435/7.92, 91.2, 366; 436/64, 503; 530/387.7, 388.22; 536/23.1

[56] References Cited

U.S. PATENT DOCUMENTS

| | | | |
|---|---|---|---|
| 4,376,110 | 3/1983 | David et al. | 435/5 |
| 4,683,202 | 7/1987 | Mullis | 435/91.2 |
| 4,946,778 | 8/1990 | Ladner et al. | 435/69.6 |

FOREIGN PATENT DOCUMENTS

| | | | |
|---|---|---|---|
| WO94/10202 | 5/1994 | WIPO | C07K 15/00 |
| WO94/11499 | 5/1994 | WIPO | C12N 15/12 |
| WO 96/41194 | 12/1996 | WIPO | G01N 33/574 |

OTHER PUBLICATIONS

Aiello, L. P. et al. (Nov. 1995). Suppression of retinal neovascularization in vivo by inhibition of vascular endothelial growth factor (VEGF) using soluble VEGF–receptor chimeric proteins. Proc. Natl. Acad. Sci. USA 92, 10457–10461.

Asano, M. et al. (Nov. 1995). Inhibitor of tumor growth and metastasis by an immunoneutralizing monoclonal antibody to human vascular endothelial growth factor/vascular permeability factor121. Cancer Research 55, 5296–5301.

Baker, P. N., Kransnow, J., Roberts, J.M., and Yeo, K.–T. (Nov. 1995). Elevated serum levels of vascular endothelial growth factor in patients with preeclampsia. Obstetrics & Gynecology 86, 815–821.

Berger, D.P., Herbstritt, L., Dengler, W. A., Marme, D., Mertelsmann, R., and Fiebig, H. H. (Oct. 1995). Vascular endothelial growth factor (VEGF) mRNA expression in human tumor models of different histologies. Annals of Oncology 6, 817–825.

Bird, R. E., Hardman, K. D., Jacobson, J. W., Johnson, S., Kaufman, B. M., Lee, S.–M., Lee, T., Pope, S. G., Riordan, G. S., and Whitlow, M. (1988). Single–chain antigen–binding proteins. Science 242, 423–426.

Bishop, J. M. (1991). Molecular themes in oncogenesis. Cell 64, 235–248.

Butler, J. E. (1981). The amplified ELISA: principles of and applications for the comparative quantitation of class and subclass antibodies and the distribution of antibodies and antigens in biochemical separates. Methods in Enzymology 73, 482–523.

Claffey, K. P. et al. (Jan. 1996). Expression of vascular permeability factor/vascular endothelial growth factor by melanoma cells increases tumor growth, angiogenesis, and experimental metastasis. Cancer Research 56, 172–181.

Cole, S. P. C., Kozbor, D., and Roder, J. C. (1985). The EBV–Hybridoma technique and its application to human lung cancer. Monoclonal Antibodies and Cancer Therapy, 77–96.

Cote, R. J., Morrissey, D. M., Houghton, A. N., Beattie, E. J. J., Oettgen, H. F., and Old, L. J. (1983). Generation of human monoclonal antibodies reactive with cellular antigens. Proc. Natl. Acad. Sci. USA 80, 2026–2030.

Ferrara, N. (1995). The role of vascular endothelial growth factor in pathological angiogenesis. Breast Cancer Research and Treatment 36(2), 127–137.

Folkman, J. (1990). What is the evidence that tumors are angiogenesis dependent? Journal of the National Cancer Institute 82, 4–6.

Folkman, J., and Shing, Y. (1992). Angiogenesis. The Journal of Biological Chemistry 267, 10931–10934.

Geursen, A. et al. (1993). Population study of T cell receptor Vb gene usage in peripheral blood lymphocytes: differences in ethnic groups. Clin. Exp Immunol. 94, 201–207.

Greenspan, N. S., and Bona, C. A. (1993). Idiotypes: structure and immunogenicity. The FASEB Journal 7, 437–444.

Houck, K. A. et al. (1991). The vascular endothelial growth factor family: identification of a fourth molecular species and characterization of alternative splicing of RNA. Molecular Endocrinology 5, 1806–1814.

Huse, W. D., Sastry, L., Iverson, S. A., Kang, A. S., Alting–Mees, M., Burton, D. R., Benkovic, S. J., and Lerner, R. A. (1989). Generation of a large combinatorial library of the immunoglobulin repertoire in phage lambda. Science 246, 1275–1281.

Huston, J. S. et al. (1988). Protein engineering of antibody binding sites: recovery of specific activity in an anti–digoxin single–chain Fv analogue produced in *Escherichia coli.* Proc. Natl. Acad. Sci. USA 85, 5879–5883.

Kendall, R. L., and Thomas, K. A. (1993). Inhibition of vascular endothelial cell growth factor activity by an endogenously encoded soluble receptor. Proc. Natl. Acad. Sci. 90, 10705–10709.

(List continued on next page.)

*Primary Examiner*—Nancy Degen
*Assistant Examiner*—William Sandals
*Attorney, Agent, or Firm*—Pennie & Edmonds LLP

[57] ABSTRACT

The invention is directed to methods of assessing the molecular stage of an disease characterized by abnormal angiogenesis. More particularly, the invention is directed to a method of determining the metastatic potential of a tumor by determining the presence of specific molecular markers. The invention is based in part on the discovery that the key marker for determining the eventual metastasis of a tumor is vascular endothelia growth factor. Knowledge of the particular markers present in a tumor condition allows the physician to tailor cancer treatment and manage the disease condition.

19 Claims, No Drawings

OTHER PUBLICATIONS

Klagsbrun, M., and Soker, S. (1993). VEGF/VPF: the angiogenesis factor found? Current Biology 3, 699–702.

Kondo, S. et al. (1993). Significance of vascular endothelial growth factor/vascular permeability factor for solid tumor growth, and its inhibition by the antibody. Bioechemical and Biophysical Research Communications 194, 1234–1241.

Kozbor, D., and Roder, J. C. (1983). The production of monoclonal antibodies from human lymphocytes. Immunology Today 4, 72–79.

Köhler, G., and Milstein, C. (1975). Continuous cultures of fused cells secreting antibodies of predefined specificity. Nature 256, 495–497.

Liotta, L. A., Steeg, P. S., and Stetler–Stevenson, W. G. (1991). Cancer metastasis and angiogenesis: an imbalance of positive and negative regulation. Cell 64, 327–336.

Matthews, W. et al. (1991). A receptor tyrosine kinase cDNA isolated from a population of enriched primitive hematopoietic cells and exhibiting close genetic linkage to c–kit. Proc. Natl. Acad. Sci. USA 88, 9026–9030.

Millauer, B., Shawver, L. K., Plate, K. H., Risau, W., and Ullrich, A. (1994). Glioblatoma growth inhibited in vivo by a dominant–negative FLK–1 mutant. Nature 367, 576–579.

Morrison, S. L., Johnson, M. J., Herzenberg, L. A., and Oi, V. T. (1984). Chimeric human antibody molecules: mouse antigen–binding domains with human constant region domains. Proc. Natl. Acad. Sci. USA 81, 6851–6855.

Mustonen, T., and Alitalo, K. (May 1995). Endothelial receptor tyrosine kinases involved in angiogenesis. Journal of Cell Biology 129, 895–898.

Neuberger, M. S., Williams, G. T., and Fox, R. O. (1984). Recombinant antibodies possessing novel effector functions. Nature 312, 604–608.

Nisonoff, A. (1991). Idiotypes: concepts and applications. Journal of Immunology 147, 2429–2438.

Plate, K. H., Breier, G., Millauer, B., Ullrich, A., and Risau, W. (1993). Up–regulation of vascular endothelial growth factor and its cognate receptors in a rat glioma model of tumor angiogenesis. Cancer Research 53, 5822–5827.

Schnürch, H., and Risau, W. (1993). Expression of tie–2, a member of a novel family of receptor tyrosine kinases, in the endothelial cell lineage. Development 119, 957–968.

Shibuya, M., Yamaguchi, S., Yamane, A., Ikeda, T., Tojo, A., Matsushime, H., and Sato, M. (1990). Nucleotide sequence and expression of a novel human receptor–type tyrosine kinase gene (flt) closely related to the fms family. Oncogene 5, 519–524.

Slamon, D. J. et al. (1989). Studies of the HER–2/neu Proto–oncogene in Human Breast and Ovarian Cancer. Science 244, 707–712.

Takahasi, Y. et al. (Sep. 1995). Expression of vascular endothelial growth fator and its receptor KDR correlates with vascularity, metastasis, and proliferation of human colon cancer. Cancer Research 55, 3964–3968.

Takeda, S.–i., Naito, T., Hama, K., Noma, T., and Honjo, T. (1985). Construction of chimaeric processed immunoglobulin genes containing mouse variable and human constant region sequences. Nature 314, 452–454.

Tischer, E., Mitchell, R., Hartman, T., Silva, M., Gospodarowicz, D., Fiddes, J. C., and Abraham, J. A. (1991). The human gene for vascular endothelial growth factor. Journal of Biological Chemistry 266, 11947–11954.

Voller, A., Bartlett, A., and Bidwell, D. E. (1978). Enzyme immunoassays with special reference to ELISA techniques. Journal of Clinical Pathology 31, 507–520.

Wang, G. L., Jiang, B.–H., Rue, E. A., and Semenza, G. L. (Jun. 1995). Hypoxia–inducible factor 1 is a basic–helix–loop–helix–pas heterodimer regulated by cellular O2 tension. Proc. Natl. Acad. Sci. USA 92, 5510–5514.

Ward, E. S., Güssow, D., Griffiths, A. D., Jones, P. T., and Winter, G. (1989). Binding activities of a repertoire of single immunoglobulin variable domains secreted from *Escherichia coli*. Nature 341, 544–546.

Weidner, N., Semple, J. P., Welch, W. R., and Folkman, J. (1991). Tumor angiogenesis and metastasis—correlation in invasive breast carcinoma. The New England Journal of Medicine 324, 1–7.

Ziegler, S. F., Bird, T. A., Schneringer, J. A., Schooley, K. A., and Baum, P. R. (1993). Molecular cloning and characterization of a novel receptor protein tyrosine kinase from human placenta. Oncogene 8, 663–670.

Bauknecht et. al.. Oncogenes, growth factors and suppressor genes and their prognostic relevance in ovarian carcinoma. Klin. Labor. (Germany). vol. 40(12):1215–1226, Dec. 1994.

Mukhopadhyay et. al.. Hypoxic induction of human vascular endothelial growth factor expression though c–Src activation. Nature. vol. 375:577–581, Jun. 15, 1995.

Wang et. al.. Chararcterization of hypoxia–inducible factor 1 and reulation of DNA binding activity by hypoxia. J. Biol. Chem. vol. 268(29):21513–21518, Oct. 15, 1993.

Goldberg et. al.. Similarities between teh oxygen–sensing mechanisms regulating the expression of vascular endothelial factor and erythropoietin. J. Biol. Chem. vol. 269(6):4355–4359, Feb. 11, 1994.

Hatva et. al.. Expressino of endothelial cell–specific receptor tyrosine kinases and growth factors in human brain tumors. Am. J. Pathol. vol. 146(2):368–378, Feb. 1995.

Plate et. al.. Up–regulation of vascular endothelial growth factor and its cognate receptors in a rat glioma model of tumor angiogenisis. Cancer Res. vol. 53:5822–5827, Dec. 1, 1993.

Guo et. al.. Vascular endothelial cell growth factor promotes tyrosine phosphorylation of mediators of signal transduction that contain SH2 domains. J. Biol. Chem. vol. 270(12):6729–6733, Mar. 1995.

Semenza et. al.. Transcriptional regulation of genes encoding glycolytic enzymes by hypoxia–inducible factor 1. J. Biol. Chem. vol. 269(38):23757–23763, Sep. 1994.

Dumont et al., 1995, "Vascularization of the Mouse Embryo: A Study of flk–1, tek, tie, and Vascular Endothelial Growth Factor Expression During Development," *Developmental Dynamics* 230:80–92.

Folkman, 1991, "Chapter 30, Antiangiogenesis," *Alternative Strategies for Biologic Therapy* : 743–753.

Folkman et al., 1987, "Angiogenic Factors," *Science* 235:442–447.

Folkman et al., 1989, "Induction of angiogenesis during the transition from hyperplasia to neoplasia," *Nature* 339:58–61.

Liu et al., 1995, "Hypoxia Regulates Vascular Endothelial Growth Factor Gene Expression in Endothelial Cells," *Circulation Research* 77:638–643.

Mustonen et al., 1995, "Endothelial Receptor Tyrosine Kinases Involved in Angiogenesis," *J. Cell Biol.* 129:895–898.

Martiny–Baron et al., 1995, "VEGF–mediated tumour angiogenesis: a new target for cancer therapy," *Current Opinion in Biotechnology* 6:675–680.

Brown et al., 1995, "Expression of Vascular Permeability Factor (Vascular Endothelial Growth Factor) and Its Receptors in Breast Cancer," *Human Pathology* 26:86–91.

Mise et al., 1996, "Clinical Significance of Vascular Endothelial Growth Factor and Basic Fibroblast Growth Factor Gene Expression in Liver Tumor," *Heptology* 23:455–464.

Ellis et al., 1995, "Vascular endothelial growth factor (VEGF) expression and alternate splicing in non–metastatic and metastatic human colon cancer cell lines," *Proc. Am. Assoc. for Cancer Res.* 36:524 (Abstract).

Toi et al., 1995, "Tumor angiogenesis in breast cancer: Its importance as a prognostic indicator and the association with vascular endothelial growth factor expression," *Breast Cancer Research and Treatment* 36:193–204.

Boocock et al., 1994, "Expression of Vascular Endothelial Growth Factor and Its Receptors flt and KDR in Ovarian Carcinoma," *Journal of the National Cancer Institute* 87:506–516.

Baban et al., 1996, "Quantitative analysis of vascular endothelial growth factor expression in chronic lymphocytic leukaemia," *International Journal of Oncology* 8:29–34.

Plate et al., 1992, "Vascular endothelial growth factor is a potential tumour angiogenesis factor in human gliomas in vivo," *Nature* 359:845–848.

Kolch et al., 1995, "Regulation and the Expression of the VEGF/VSP and Its Receptors: Role in Tumor Angiogenesis," *Breast Cancer Res. and Treatment* 36:139–155.

Larcher et al., 1996, "Up–Regulation of Vascular Endothelial Growth Factor/Vascular Permeability Factor in Mouse Skin Carcinogenesis Correlates with Malignant Progression State and Activated H–ras Expression Levels[1]," *Cancer Research* 56:5391–5396.

U.S. application No. 08/193,829, Ullrich et al., filed Feb. 9, 1994.

U.S. application No. 08/436,065, Plowman, filed May 5, 1995.

U.S. application No. 08/621,724, Hirth et al., filed Mar. 21, 1996.

METHOD FOR MOLECULAR DIAGNOSIS OF TUMOR ANGIOGENESIS AND METASTASIS

1. INTRODUCTION

The present invention relates to methods for molecularly staging a cancerous condition so as to design appropriate patient treatment. Specifically, the present invention is directed at assays for assessing the angiogenic phenotype of a carcinoma through the use of molecular markers common to all types of metastatic solid tumors, specifically vascular endothelial growth factor and its cognate receptors, as well as other prognostic molecular markers.

2. BACKGROUND OF THE INVENTION

Knowledge of a tumor's metastatic potential is important in developing cancer treatments which maximize patient survival and quality of life. The most aggressive treatment regimes should be reserved for those patients at highest risk for rapid tumor growth and metastasis. Therefore, much effort has focused on identifying markers characteristic of the metastatic potential of carcinomas.

One type of marker for the metastatic stage of a cancer is the presence of an oncogene allele. For example, a gene associated with over 30% of mammary carcinoma and ovarian carcinoma has been identified as the neu/HER2/c-erbB2 proto-oncogene, The degree of amplification of the proto-oncogene and the overexpression of its protein product were found to correlate with the severity of disease and poor prognosis. Slamon et al., *Science* 244:707–712 (1989). In addition, aberrant alleles of the ras and myc gene families have been shown to be involved in the progression of human cancers, and some researchers have speculated they would be useful as prognostic indicators. Field, J. K. et al., *Anticancer Res.* 10: 1–22 (1990). Moreover, transfection of H-ras family oncogenes and mutant p53 alleles into recipient cells will induce metastatic potential. Liotta, L. A. et al., *Cell* 64: 327–36 (1991).

However, a major problem with the use of these oncogene markers is that these factors are not predictive for all types of tumors. Instead, these markers are specific to the tissue or type of tumor in which they have arisen, and will likely not have broad applicability for all types of metastatic carcinomas.

A growing body of evidence indicates that angiogenesis is essential to the progression of cancer. Angiogenesis is the sprouting of new capillaries from preexisting blood vessels. Normally, angiogenesis in mammals is confined to the reproductive system, embryogenesis and development, and repair after injury. However, angiogenesis can also occur in pathological conditions such as cancer, retinal neovascularization, neovascularization in atherosclerotic plaques, hemangiomas, arthritis, and psoriasis. See Folkman, J. *New England J. of Med.* 333:1757–63 (1995).

Without vascularization, tumors may remain for years as small (less than a few millimeters) asymptomatic lesions. Weidner et al. New England J. of Med. 324:1–8 (1991). Tumors which become vascularized receive increased oxygen and nutrients through perfusion. Thus, tumors which are vascularized can grow and proliferate. A tumor must constantly stimulate the growth of new capillary blood vessels in order for it to continue to grow. Additionally, angiogenesis allows the tumor cells access to the host animal's circulatory system. The new blood vessels provide a gateway for tumor cells to enter the circulation and metastasize to distant sites. Folkman, *J. Natl. Cancer Inst.* 82:4–6 (1990); Klagsbrunn and Soker, *Current Biology* 3:699–702 (1993); Folkman, J., *J. Natl., Cancer Inst.* 82:4–6 (1991); Weidner et al., *New Engl. J. Med.* 324:1–5 (1991).

In fact, the extent of neovascularity is strongly correlated with metastases in primary breast carcinoma, bladder cancer, prostrate cancer, non-small cell lung cancer, cutaneous melanomas, and uterine cervix carcinoma. Reviewed in Ferrara, N., Breast Cancer Research and Treatment 36: 127–137 (1995). In these studies, tumor specimens were histologically analyzed and the number of microvesicles manually counted. The extent of tumor mass vascularization was found to be an independent predictor of the metastatic potential, and more reliable than other prognostic markers.

These results have led researchers to speculate that tumor vascularization could be used as a diagnostic tool to predict metastasis. However, counting of microvesicles in tumor specimens, besides being labor-intensive, is a qualitative art. The method requires considerable technical training in order to obtain reliable and reproducible results. Some groups have reported difficulties in reproducing the method. Wiedner, N., *Amer. J. Path.* 147: 9–19 (1995). Additionally, the process of preparing specimens for histology and counting vesicles is time consuming. Therefore, the application of this technique has been limited generally to research purposes.

There thus remains a need for a rapid and objective technique that could be used generally in the clinic to assess tumor vascularization and thus predict the metastatic potential of a tumor.

Several investigators have speculated that one may be able to measure angiogenic activity in patients by quantitating the presence of angiogenic proteins. There are twelve known angiogenic proteins whose presence could potentially indicate angiogenesis. Folkman J. *New England J. of Med.* 333:1757–63 (1995). Of these factors, those most commonly found associated with tumors are basic fibroblast growth factor (bFGF), vascular endothelial growth factor (VEGF), insulin growth factor-2, platelet derived growth factor, and colony stimulating factors. Other factors which are candidates for angiogenic and metastatic markers are urokinase-type plasminogen activator and plasminogen activator inhibitor-1, as well as a variety of collagenases and urokinases. Wiedner, N., *Amer. J. Path.* 147: 9–19 (1995).

However, to choose a generally applicable marker for angiogenesis and metastasis, it is desirable that the key factor in this process be identified. At present, the factor or factors causing tumor angiogenesis have yet to be determined. Id. It has been speculated that bFGF and VEGF act synergistically. Id. Levels of bFGF were elevated in the urine of approximately 37% of a wide range of cancer patients. Similarly, bFGF was also elevated in the serum of 10% of these patients. Highest levels of bFGF were found in patients with metastatic disease. Reviewed in Folkman J. *New England J. of Med.* 333:1757–63 (1995). bFGF was also abnormally high in the cerebrospinal fluid of children with brain tumors, and these high levels correlated with density of microvessels in the tumor specimens. Id.

On the other hand, different investigators have found that transfection of VEGF expression plasmids into melanoma cell lines increases their capacity for growth, angiogenesis, and metastasis when injected into mice. Claffey, K. et al., *Cancer Res.* 56: 172–81 (1996). A correlation of the semi-quantitative level of immunoreactive VEGF protein in tumor specimens with the extent of microvesicular development and metastatic potential has been shown in colon carcinoma patients. Takahashi, Y. et al., *Cancer Res.* 55: 3964–68

(1995). This study only subjectively assessed the level of VEGF staining in histochemical sections. Further, certain inconsistencies in their data led these experimenters to hypothesize that VEGF may not always be the factor responsible for angiogenesis. In a study by another group, experimental xenografts of human tumor cells in mice indicated that higher levels of vascularization and VEGF RNA were found in those xenografted tumors derived from patients with a lower survival rate. Berger, D. P. et al., *Annals. of Oncology* 6: 817–825 (1995). However, this study did not contain a negative control, and was a retrospective analysis of tumor cells which had been serially passaged in nude mice up to 8 to 12 times, thus raising the possibility that tumor characteristics had changed.

Finally, some investigators assert that no one mechanism or factor is responsible for the development of tumor angiogenesis. While tumors might release angiogenic molecules, they assert that it is unclear how this release of factors differs from non-angiogenic cells. Instead, these investigators believe that the onset of angiogenic activity is determined by the balance of factors which are present. Folkman, J. and Shing, Y. *J. Biol. Chem.* 267: 10931–34 (1992).

Thus, a controversy exists over which are the best markers for tumor angiogenesis and metastatic potential. At best, there is a debate over the marker or markers which will be universally applicable to all types of solid tissue carcinomas. The present invention provides a resolution for this debate, completely eliminates the need for laborious histological analysis of tumor specimens, and provides a generally applicable and rapid method for determining the metastatic potential of solid tissue carcinoma in a patient.

3. SUMMARY OF THE INVENTION

Accordingly, the object of the present invention is to provide an objective molecular diagnostic tool to characterize and stage the progression of a disease condition involving abnormal angiogenesis.

In a preferred embodiment of the invention, a cancerous condition is monitored in a human subject by assaying the expression of specific molecular markers. However, any disease characterized by abnormal angiogenesis may be molecularly staged using the method of the invention, such as retinal neovascularization, neovascularization in atherosclerotic plaques, hemangiomas, arthritis, and psoriasis. The information acquired through this diagnostic tool is used by the physician to design treatment protocols for which to treat and manage the disease condition.

In one aspect of the invention, the level of VEGF expression in a human with a cancerous condition is detected and monitored. Because abnormal increased expression of VEGF by a tumor triggers the onset of angiogenesis, the level of VEGF is a molecular marker for the progression of the cancerous condition. The presence of VEGF may be assayed in a body fluid, through tissue biopsy, or in tissue specimens obtained through surgical debulking.

In another aspect of the invention, the expression of receptor proteins in the endothelium cells associated with the tumor which respond to VEGF and other factors is also detected and monitored. These receptor proteins include but are not limited to KDR/flk-1, flt-1, and/or tek/tie-2. Co-expression of VEGF and any of these receptor proteins is also indicative of a tumor able to undergo increased growth and metastasis. Identification of the particular receptor involved in the angiogenic pathway is important in determining which treatment will be most effective and selective for inhibiting angiogenesis.

A further aspect of the invention is to assay the presence of various other molecular markers indicative of disease progression. For example, expression at the site of a tumor of hypoxia induced factor (HIF) in the absence of VEGF or KDR/flk-1 expression would indicate that the tumor has not progressed to a stage where treatment with angiogenesis inhibiting factors would be necessary. On the other hand, expression of VEGF and KDR/flk-1 in conjunction with an oncogene and/or a mutation in a tumor suppressor gene would define a malignant tumor and dictate a more aggressive treatment regime.

4. DETAILED DESCRIPTION OF THE INVENTION

4.1 Morphological and Molecular Events During Cancer Progression

Tumors may persist for years as small asymptomatic carcinomas in which, although cells are rapidly dividing, the rate of cell death equals the rate of cell proliferation. Within the necrotized tumor mass, increased interstitial pressure and hypoxic conditions occur. Recently, it has been found that hypoxic conditions will induce the expression of hypoxia inducing factor (HIF), a cellular transcription factor involved in the expression of VEGF. HIF-1 has been cloned and identified as a heterodimeric DNA binding protein. Wang, G. L. et al., *Proc. Natl. Acad. Sci. USA* 92: 5510–14 (1995), which is incorporated herein by reference in its entirety.

During the development of a metastatic tumor, some cells in the tumor mass "switch" to an angiogenic phenotype and neovascularization occurs. This "switch" is in part due to hypoxia and the induction of HIF; however, production of HIF alone is insufficient to trigger the expression of VEGF. Tumors may produce HIF but not VEGF and remain quiescent. The invention is based in part on the discovery that VEGF may be used as the key molecular marker for tumor metastasis. Only those tumors which can produce VEGF in response to hypoxia and the production of HIF will become capable of continued growth and eventually metastasis. Thus, VEGF, not HIF, is the key determinant of whether the tumor has switched to the angiogenic phenotype.

VEGF is a heparin-binding, homodimeric glycogprotein of about 45 kD. It has been isolated from a variety of sources and cell lines, and the gene cloned from human cells as well as those of other species. See Tisher, E. et al., *J. Biol. Chem.* 266: 11947–54 (1991) and Houck, K. A. et al., *Mol. Endocrinol.* 5: 1806–14 (1991); both of which papers are incorporated by reference in their entirety herein. The VEGF gene transcript is alternatively spliced into at least four different molecular species of 121, 165, 189, and 206 amino acids. $VEGF_{165}$ is the most common form, and is available commercially as a recombinantly produced protein product. (R&D Systems, Minneapolis, Minn.) The biochemical properties of this product correspond closely to those of $VEGF_{165}$ isolated from naturally occurring sources.

Release of VEGF by the tumor mass stimulates angiogenesis in adjacent endothelial cells. Normally, capillary endothelial cells turn over extremely slowly (thousands of days) and are kept quiescent through contact with specialized cells, called pericytes. When VEGF is expressed by the tumor mass, endothelial cells closely adjacent to the VEGF+ tumor cells will up-regulate expression of VEGF receptor molecules KDR/flk-1 and/or flt-1.

Both the KDR/flk-1 and flt-1 are receptor tyrosine kinase proteins with high specificity for VEGF. Upon binding of their ligand, these receptors dimerize and transduce an intracellular signal through tyrosine phosphorylation. The KDR/flk-1 receptor tyrosine kinase was cloned from human cells and the cDNA reported by Matthews, W. et al., *Proc. Natl. Acad. Sci. USA* 88: 9026–30, incorporated herein in its entirety by reference. Only later, when a similar receptor was identified and characterized in murine cells, was the ligand for the KDR/flk-1 receptor identified as VEGF. See co-pending U.S. application Ser. No. 08/193,829, filed Feb. 9, 1994, which is incorporated in its entirety herein by reference.

VEGF is also the ligand for the flt-1 receptor. The nucleotide sequence of the human flt-1 protein was reported by Shibuya, M. et al., *Oncogene* 5:519–24 (1990), which is incorporated herein in its entirety by reference.

Binding of VEGF to its cognate VEGF receptors on endothelial cells initiates a chemotaxic effect in these cells through signal transduction. New capillaries sprout from the endothelial vessels towards the VEGF+ tumor cells. During angiogenesis, the endothelial cells rapidly proliferate by dividing up to every five days.

Soon after the stimulation of endothelial cells by the binding of VEGF to its cognate receptors occurs, the orphan receptor tek/tie-2 is expressed by the endothelial cells developing into new capillaries. Since tek/tie-2 is expressed at the tip of invading capillaries and in more advanced vessels, it is likely that this receptor participates in migration, proliferation, and maintenance of the new capillary cells. Indeed, analysis of tyrosine kinase receptor expression during angiogenesis in the developing mouse brain showed tek/tie-2 expression approximately twelve hours after KDR/flk-1 receptor was expressed. Cloning of the human gene for tek/tie-2 is described in Ziegler, S. F. et al., *Oncogene* 8: 663–70 (1993), which is incorporated in its entirety by reference herein.

Other receptors which have been observed during angiogenesis, but whose role in this process is still unclear, are the flt-4 receptor, fibroblast growth factor receptors, platelet derived growth factor $\beta$ receptor, epidermal growth factor receptor, and the Met oncogene. Reviewed in Tuija, M. and Alitalo, K., *J. Cell Biol.* 129: 895–898.

The present invention uses knowledge of the molecular events associated with onset of angiogenesis as outlined above in a method for assessing the metastatic stage of a carcinoma and devising appropriate treatment. In particular, the key to the method of the invention is the realization that only those tumors which express VEGF have the capacity to grow and metastasize.

In one aspect of the invention, a sample of a tumor from a human is molecularly characterized for the presence of the VEGF messenger RNA or protein using the techniques described below. The sample may also be characterized for expression of the factors HIF-1, KDR/flk-1, flt-1, and/or tek/tie-2, using similar techniques. The presence of additional angiogenic factors and receptors, as well as the presence of oncogene alleles may also be assessed. The sample may be obtained by biopsy, needle biopsy, or after surgical debulking, and may be analyzed histologically or as a cellular lysate. Although the presence of any VEGF is indicative of angiogenic activity, the level of VEGF with regard to a control marker such as glucose-6-phosphate dehydrogenase, or any other "housekeeping protein" or RNA species, may be compared to that in a normal tissue sample.

A major advantage of the present invention is that the need to manually count blood vessels in a sample is eliminated (although it may still be accomplished). The expression of HIF-1 is a marker for hypoxia occurring in and near the tumor mass. Thus, HIF-1 may be used as an indication that the necrotic, hypoxic portion of the tumor has been obtained. If VEGF is also present, this would indicate that the tumor has "switched" to the angiogenic phenotype and that metastasis is possible. The presence of additional receptor tyrosine kinases involved in angiogenesis provides further information regarding the stage of angiogenesis reached by the tumor and potential targets for therapeutic treatments.

The sample may also be analyzed for the expression of any of the large number of oncogenes known to be involved in cancer, including but not limited to ABL, ERBB-1, NEU, GIP, GSP, MYC, L-MYC, H-RAS, K-RAS, N-RAS, RET, ROS, K-SAM, SIS, SRC, and TRK. Reviewed in Bishop, J. M. *Cell* 64: 235–48 (1991), incorporated by reference herein in its entirety. Additionally, the expression of tumor suppressor genes may also be assessed, such as RB1, p53, WT1, DCC, NF1, FAP, and MEN-1.

In another aspect of the invention, a body fluid, for example, blood, serum, urine, lymph, and/or cerebrospinal fluid, is assayed for elevated concentrations of VEGF. Alternatively, a detectably labeled ligand for VEGF, such as a radioactively labeled antibody specific for VEGF, or a labeled protein containing the extracellular domain of a VEGF receptor molecule, is introduced into the body of a human and the localization of the labeled ligand is detected by standard procedures such as CAT scan, MRI, Geiger counter, or other equivalent device.

Once the molecular profile of a tumor is determined using the methods of the invention, the physician can design appropriate therapies to optimize both effectiveness of cancer treatment and quality of patient life. Thus, using the knowledge obtained via the methods of the invention, management of the cancerous condition may be improved in order to transform an acute deadly disease into a chronic condition.

4.2 Assays for Molecular Events During Angiogenesis

A variety of methods can be employed for the diagnostic and prognostic evaluation of tumor angiogenesis and metastasis, and for the identification of subjects having a predisposition to such conditions.

Such methods may, for example, utilize reagents such as VEGF nucleotide sequences and VEGF antibodies, as described herein. Specifically, such reagents may be used, for example, for: (1) the detection of the presence or over-expression of VEGF mRNA relative to the non-carcinogenic tissue state; (2) the detection of an over-abundance of VEGF protein relative to the non-carcinogenic tissue state; (3) the detection of hypoxic conditions in the tumor mass; (4) the detection of the expression of VEGF tyrosine kinase receptors and other angiogenic receptors in adjacent endothelial tissues; and (5) the detection of the expression of oncogenes.

The methods described herein may be performed, for example, by utilizing pre-packaged diagnostic kits comprising at least one specific VEGF nucleotide sequence or VEGF antibody reagent described herein, which may be conveniently used, e.g., in clinical settings, to diagnose patients at risk for tumor angiogenesis and metastasis.

For the detection of VEGF gene expression, any cell type or tissue in which the VEGF gene is expressed, such as, for example, tumor cells, may be utilized. For the detection of VEGF proteins, any cell type or tissue in which the VEGF gene is expressed may also be used, as well as any cells which are known to express VEGF receptors, such as endothelial cells. In addition, the presence of VEGF proteins may be assayed in any body fluid in continuity with the tumor mass. For example, in the case of brain tumors, cerebrospinal fluid may preferably be utilized. For other types of tumors, blood, serum, and/or urine may be analyzed.

Nucleic acid-based detection techniques are described below in Section 4.2.1. Peptide detection techniques are described below in Section 4.2.2. Although these techniques are all described with regard to detecting VEGF expression, the key marker used in the method of the invention, all these techniques may also be used for detecting any other molecular marker associated with angiogenesis. For example, these techniques may be used to determine the pattern and level of expression of HIF-1 and of receptor proteins KDR/flk-1, flt-1, and tek/tie-2, as well as other angiogenic proteins.

Further, the expression of different oncogene alleles may be assessed using these methods. The additional information obtained regarding the expression of other markers will assist in designing appropriate therapies to inhibit angiogenesis and/or tumor proliferation tailored to the molecular stage of the cancer in a particular patient.

4.2.1 DETECTION OF THE VEGF GENE AND TRANSCRIPTS

The level of VEGF gene expression can be assayed by detecting and measuring VEGF transcription. Nucleic acid from any cell can be used as the starting point for such assay techniques, and may be isolated according to standard nucleic acid preparation procedures which are well known to those of skill in the art. For example, RNA from a tumor specimen suspected to express the VEGF gene may be isolated and tested utilizing hybridization or PCR techniques such as are described below. The isolated cells can be derived from cell culture or from a patient. The analysis of cells taken from culture may be useful to test the effect of compounds on the expression of the VEGF gene. Such analyses may reveal both quantitative and qualitative aspects of the expression pattern of the VEGF gene, including activation or inactivation of VEGF gene expression.

Such diagnostic methods for the detection of VEGF gene transcripts can involve for example, contacting and incubating nucleic acids, such as RNA or cDNA generated from RNA, obtained from a sample, with one or more labeled nucleic acid reagents including recombinant DNA molecules or in vitro transcribed anti-sense RNA probes, under conditions favorable for the specific annealing of these reagents to their complementary sequences within the VEGF gene. Preferably, the lengths of these nucleic acid reagents are at least 15 to 30 nucleotides. After incubation, all non-annealed nucleic acids are removed from the nucleic acid:VEGF molecule hybrid. The presence of nucleic acids which have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 4.1 are easily removed. Detection of the remaining, annealed, labeled VEGF nucleic acid reagents is accomplished using standard techniques well-known to those in the art. The extent to which labeled VEGF gene sequences have annealed to the sample can be compared to the annealing pattern expected from a normal cell or tissue in order to determine whether VEGF gene expression is present.

Alternative diagnostic methods for the detection of VEGF gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained only normal levels of the VEGF gene transcript in order to determine whether VEGF gene expression is up-regulated.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the VEGF nucleic acid sequences. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such VEGF gene expression assays "in situ", i.e., directly upon tissue sections (fixed and/or frozen) of patient tissue obtained from biopsies or resections, such that no nucleic acid purification is necessary. Nucleic acid reagents such as those described in Section 4.1 may be used to design probes and/or primers for such in situ procedures (See, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the VEGF gene.

4.2.2 DETECTION OF VEGF PROTEINS

Antibodies directed against VEGF proteins or conserved variants or peptide fragments thereof may be used as tumor angiogenesis and metastasis diagnostics and prognostics, as described herein. Such diagnostic methods, may be used to detect abnormalities in the level of VEGF gene expression, or abnormalities in the structure and/or temporal, tissue, cellular, or subcellular location of the VEGF, and may be performed in vivo or in vitro, such as, for example, on biopsied tissue. Antibodies may also be used as a method for inhibition of abnormal VEGF activity. Thus, such antibodies may be utilized as part of cancer treatment methods.

Antibodies that may be used in the methods of the invention include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

For the production of antibodies, various host animals may be immunized by injection with VEGF, truncated VEGF polypeptides, and VEGF fusion proteins. VEGF may be isolated from natural sources using well known techniques, or may be recombinantly produced. Recombinant VEGF is commercially available from R&D Systems, MN.

Fusion proteins of VEGF are also suitable as antigens. A well known system amenable for the production of fusion proteins with coding sequence from almost any gene is that using the PGEX vectors (Pharmacia, Piscataway, N.J.). A coding region of choice is inserted into a bacterial expression vector in-frame and downstream of an open reading frame encoding glutathione-S-transferase (GST). The resulting vector is transformed into *E. coli*; induction of expression from the vector results in the production of a GST-fusion protein which may be easily purified from a cell lysate on glutathione agarose beads (Pharmacia, Piscataway, N.J.). The purified fusion protein may be used directly as an antigen, or the GST moiety may be cleaved from the fusion protein and the peptide encoded by the inserted sequences used as an immunogen.

Host animals for production of antibodies may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, *Nature* 256:495–497; and U.S. Pat. No. 4,376,110), the human B-cell hybridoma technique (Kosbor et al., 1983, *Immunology Today* 4:72; Cole et al., 1983, *Proc. Natl. Acad. Sci. USA* 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, *Proc. Natl. Acad. Sci. USA*, 81:6851–6855; Neuberger et al., 1984, *Nature*, 312:604–608; Takeda et al., 1985, *Nature*, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, *Science* 242:423–426; Huston et al., 1988, *Proc. Natl. Acad. Sci. USA* 85:5879–5883; and Ward et al., 1989, *Nature* 334:544–546) can be adapted to produce single chain antibodies against VEGF proteins. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, *Science*, 246:1275–1281) to allow rapid and easy identification of monoclonal Fab fragments with the desired specificity.

Antibodies to VEGF can, in turn, be utilized to generate anti-idiotype antibodies that "mimic" VEGF, using techniques well known to those skilled in the art. (See, e.g., Greenspan & Bona, 1993, *FASEB J.* 7(5):437–444; and Nissinoff, 1991, *J. Immunol.* 147(8):2429–2438). For example antibodies which bind to VEGF and competitively inhibit the binding of VEGF to the VEGF receptors can be used to generate anti-idiotypes that "mimic" VEGF and, therefore, bind and neutralize the receptors. Such neutralizing anti-idiotypes or Fab fragments of such anti-idiotypes can be used in therapeutic regimens to neutralize VEGF activity and inhibit angiogenesis.

Additionally, any VEGF receptor fusion protein or VEGF receptor conjugated protein whose presence can be detected, can be administered. Preferably, a soluble extracellular domain of a VEGF receptor may be used, such as the endogenously encoded sflt-1 receptor lacking the transmembrane and intracellular kinase domains. Kendall R. and Thomas, K., *Proc. Natl. Acad. Sci. USA* 90: 10705–10709 (1993). For example, VEGF receptor fusion or conjugated proteins labeled with a radio-opaque or other appropriate compound can be administered and visualized in vivo, as discussed above for labeled antibodies. Further, such VEGF receptor fusion proteins can be utilized for in vitro diagnostic procedures.

Antibodies directed to VEGF can be used in vivo to detect the pattern and level of expression of the VEGF in the body. Such antibodies can be labeled, e.g., with a radio-opaque or other appropriate compound and injected into a subject in order to visualize binding to the VEGF expressed in the body using standard methods such as X-rays, CAT-scans, or MRI. Labeled antibody fragments, e.g., the Fab or single chain antibody comprising the smallest portion of the antigen binding region, are preferred for this purpose to promote crossing the blood-brain barrier.

Alternatively, immunoassays or fusion protein detection assays, as described above, can be utilized on biopsy and autopsy samples in vitro to permit assessment of the expression pattern of the VEGF. Such assays are not confined to the use of antibodies that define VEGF, but can include the use of antibodies directed to epitopes of any of the domains of HIF-1, KDR/flk-1, flt-1, and tek/tie-2. The use of each or all of these labeled antibodies will yield useful information regarding the stage of tumor development.

The tissue or cell type to be analyzed will generally include those which are suspected to express the VEGF gene, such as tumor cells, endothelial cells which contain binding sites for the VEGF protein, and body fluids. A description of a VEGF assay suitable for quantitation of VEGF in a body fluid is described in Baker, P. D. et al., *Obstetrics & Gynecology* 86: 815–821 (1995), which is incorporated herein in its entirety by reference. The protein isolation methods employed herein may, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety. The isolated cells can be derived from cell culture or from a human. The analysis of cells taken from culture may be useful to test the effect of compounds on the expression of the VEGF gene.

The antibodies (or fragments thereof) or VEGF receptor fusion or conjugated proteins useful in the present invention may, additionally, be employed histologically, as in immunofluorescence, immunoelectron microscopy or non-immuno assays, for in situ detection of VEGF proteins or conserved variants or peptide fragments thereof.

In situ detection may be accomplished by removing a histological specimen from a patient, and contacting it with a labeled antibody or fusion protein of the present invention. The antibody (or fragment) or fusion protein is preferably applied by overlaying the labeled antibody (or fragment) onto a biological sample. Through the use of such a procedure, it is possible to determine not only the presence of the VEGF protein, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for VEGF proteins or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying VEGF proteins or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled VEGF antibody or VEGF receptor fusion protein. The solid phase support may then be washed with the buffer a second time to remove unbound antibody or fusion protein. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of VEGF antibody may be determined according to well known methods. Those skilled in the art will be able to determine operative and optimal assay conditions for each determination by employing routine experimentation.

With respect to antibodies, one of the ways in which the VEGF antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, *Microbiological Associates Quarterly Publication*, Walkersville, Md.); Voller, A. et al., 1978, *J. Clin. Pathol.* 31:507–520; Butler, J. E., 1981, Meth. Enzymol. 73:482–523; Maggio, E. (ed.), 1980, *Enzyme Immunoassay*, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect VEGF through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

4.3 Detection of Additional Molecular Markers Associated With Cancer and Metastasis As noted above, the nucleic acid and protein detection techniques detailed above for the analysis of the presence of VEGF in a tumor may also be used to assay for the expression of various other factors associated with the angiogenic phenotype, including but not limited to HIF, KDR/flk-1, flt-1, tek/tie-2, or any one of a variety of receptor tyrosine kinases involved in angiogenesis. Additionally, one may assay for the expression of an oncogene allele or the absence of a tumor suppressor gene product using the techniques detailed above.

In a variation of the methods detailed above to detect VEGF protein, one may detect the presence of a VEGF receptor protein, such as KDR/flk-1 and/or flt-1 by using VEGF which has been detectably labeled or fused to a protein whose presence may be easily determined. For example, VEGF may be radioactively labeled with $^{35}$S-containing amino acids during recombinant synthesis. Alternatively, VEGF may be recombinantly produced as a fusion protein comprising an immunoglobulin constant domain using techniques well known to those of skill in the art.

A complete profile of the receptor tyrosine kinase receptors present in a sample, including KDR/flk-1, flt-1, tek/tie-2 as well as any other receptor tyrosine kinase receptors, may be determined using the transcript imaging technique described fully in U.S. application Ser. No. 08/436,065, filed May 5, 1995 now U.S. Pat. No. 5,830,648, the disclosure of which is incorporated herein by reference in its entirety.

4.4. Molecular Profiling of the Tumor to Design Cancer Treatment and Choose Angiogenic Inhibitors Using the information derived from the method of the invention detailed above, the physician can then design appropriate treatment tailored to the molecular stage of the cancerous condition in a patient. In the first stage of a carcinoma, cells begin to rapidly proliferate. A small tumor is formed. In the absence of a constant flow of additional nutrients and oxygen to the growing tumor mass, cells begin to die at the site of the tumor as rapidly as they divide. During this stage, hypoxic conditions within the necrotized tumor mass occur and can be detected by the induction of HIF-1. However, in the absence of VEGF, angiogenesis will not occur and the tumor mass will remain small and isolated from the circulatory system. When a sample from this tumor is assayed using the methods of the invention, the cells will be found to express HIF-1, but will not express VEGF. This tumor stage is pre-angiogenic and has not progressed to a metastatic phenotype. Thus, treatment of the tumor, if any, should be limited to the tumor site, and the patient monitored at future intervals.

If the tumor cells isolated from a patient are shown to express VEGF using the diagnostic methods of the invention, this patient is a candidate for anti-angiogenic therapy. Considerable evidence has accumulated that if angiogenesis is inhibited, tumor growth and metastasis will also be inhibited. See, for example, Asano, M., et al., *Cancer Research* 55: 5296–5301 (1995); Kondo, S. et al., *Biochem. Biophys. Res. Comm.* 194: 1234–41 (1993); and Millauer, B. et al., *Nature* 367: 576–79 (1994).

Suitable anti-angiogenic drugs may be chosen from those known or believed to generally inhibit angiogenesis, such as interferon-α2a, thalidomide, minocycline, a synthetic analogue of fumagillin TNP-470, interleukin-12, metalloproteinase inhibitors, and platelet factor 4 for example, as described in Folkman J. *New England J. of Med.* 333:1757–63 (1995). Further, the activity of VEGF can be directly inhibited by specific monoclonal antibodies which bind and neutralize VEGF such as those described in Asano, M., et al., *Cancer Research* 55: 5296–5301 (1995), or by using a truncated VEGF receptor such as the endogenously encoded sflt-1 receptor lacking the transmembrane and intracellular kinase domains. Kendall R. and Thomas, K., *Proc. Natl. Acad. Sci. USA* 90: 10705–10709 (1993).

Moreover, knowledge of the specific receptors involved in a cancerous condition, in addition to VEGF, allows one to target those receptors for drug therapy. For example, if KDR/flk-1 is known to be involved in the carcinoma, one may utilize the compounds described in co-owned and co-pending U.S. Application Attorney Docket No. 7683-114, filed Mar. 21, 1996, which is incorporated herein by reference in its entirety, to specifically inhibit the KDR/flk-1 receptor.

In addition, if VEGF is present, this is indicative that the tumor has progressed to the stage where metastasis may have occurred. Depending upon the particular tumor profile obtained, the physician may want to combine anti-angiogenic therapy with an aggressive full body treatment such as chemotherapy. The identification of known tumor oncogenes and prognostic indicators of metastasis and proliferation will assist in determining the aggressiveness of the treatment regime chosen by the physician.

EQUIVALENTS

The foregoing written specification is considered to be sufficient to enable one skilled in the art to practice the invention. Indeed, various modifications of the above-described methods for carrying out the invention which are apparent to those skilled in the field of molecular biology or related fields are intended to be within the scope of the following claims.

What is claimed is:

1. A method of detecting metastasis at a site distal from a primary tumor in a human comprising:
   a) assaying a sample of cells from the human for the presence of VEGF transcripts; and
   b) determining the existence of metastasis wherein the abnormal presence of VEGF transcripts in cells distal from the primary tumor indicates the presence of metastasis in the human.

2. The method of claim 1 wherein the presence of VEGF transcripts is measured by specific hybridization of RNA from the cells to a labeled complementary nucleic acid.

3. The method of claim 1 wherein the presence of VEGF transcripts is measured by polymerase chain reaction.

4. The method of claim 1 further comprising assaying the sample for the presence of VEGF protein.

5. The method of claim 1 further comprising assaying the sample for the expression of hypoxia induced factor 1.

6. The method of claim 1 further comprising assaying for the abnormal expression of an oncogene.

7. The method of claim 1 wherein the cells are tumor cells.

8. The method of claim 7 wherein the tumor cells are obtained through a biopsy.

9. The method of claim 1 further comprising assaying the sample for the expression of tyrosine kinase receptors involved in angiogenesis.

10. The method of claim 9 wherein the tyrosine kinase receptor is chosen from the group consisting of the KDR/flk-1 receptor, the flt-1 receptor, and the tek/tie-2 receptor.

11. A method of detecting metastasis at a site distal from a primary tumor in a human consisting of:
   a) assaying a sample of tissue or fluid from the human for the presence of VEGF protein in the sample; and
   b) determining the existence of metastasis by the presence of VEGF protein, wherein the abnormal presence of VEGF protein at a site distal from the primary tumor indicates the presence of metastasis in the human.

12. The method of claim 11 wherein the sample is obtained through a biopsy.

13. The method of claim 11 wherein the fluid is blood.

14. The method of claim 11 further comprising assaying the sample for the expression of hypoxia induced factor.

15. The method of claim 11 further comprising assaying for the expression of an oncogene.

16. The method of claim 11 wherein the presence of VEGF is determined using an anti-VEGF antibody.

17. The method of claim 16 wherein the anti-VEGF antibody is used in an ELISA assay.

18. The method of claim 11 further comprising assaying the sample for the expression of tyrosine kinase receptors involved in angiogenesis.

19. The method of claim 18 wherein the tyrosine kinase receptors are chosen from the group consisting of the KDR/flk-1 receptor, the flt-1 receptor, and the tek/tie-2 receptor.

* * * * *